United States Patent
Magovern et al.

(10) Patent No.: US 6,221,079 B1
(45) Date of Patent: Apr. 24, 2001

(54) METHOD AND APPARATUS FOR VESSEL REPAIR IN A PATIENT

(75) Inventors: James A. Magovern, Pittsburgh; Wayne P. Griffin, Cranberry; David W. Kletzli, Clinton; Michael Szwerc, Allison Park; Dennis R. Trumble, Pittsburgh, all of PA (US)

(73) Assignee: Cardiac Assist Technologies, Inc., Pittsburgh, PA (US)

( * ) Notice: Subject to any disclaimer, the term of this patent is extended or adjusted under 35 U.S.C. 154(b) by 0 days.

(21) Appl. No.: 09/385,577

(22) Filed: Aug. 31, 1999

(51) Int. Cl.[7] ....................................... A61F 11/00
(52) U.S. Cl. .......................... 606/108; 606/198; 606/191
(58) Field of Search ...................... 606/108, 191, 606/194, 195, 198, 153, 193, 197; 604/96, 104; 623/1.11, 1.13, 1.28

(56) References Cited

U.S. PATENT DOCUMENTS

| | | | |
|---|---|---|---|
| 4,434,797 | * 3/1984 | Silander | 606/108 |
| 5,330,490 | * 7/1994 | Wilk et al. | 606/153 |
| 5,476,506 | * 12/1995 | Lunn | 623/1.11 |
| 5,522,881 | * 6/1996 | Lentz | 623/1.11 |
| 5,669,930 | * 9/1997 | Igarashi | 606/191 |
| 5,941,908 | * 8/1999 | Glodsteen et al. | 623/1.11 |
| 6,010,529 | * 1/2000 | Herweck et al. | 623/1.11 |
| 6,071,297 | * 6/2000 | Salahieh et al. | 606/108 |

* cited by examiner

Primary Examiner—Philogene Pedro
(74) Attorney, Agent, or Firm—Ansel M. Schwartz

(57) ABSTRACT

An apparatus for repairing a vessel in a patient. The apparatus includes a graft. The apparatus includes a mechanism for compressing the vessel to the graft and holding the vessel to the graft. A method of repairing a vessel of a patient. The method includes the steps of placing a first end of a graft in contact with a first side of the vessel. Then there is the step of placing a second side of the graft in contact with the second side of the vessel. Next there is the step of compressing the first side of the vessel against the first end. Then there is the step of compressing the second side of the vessel against the second end.

19 Claims, 2 Drawing Sheets

METHOD AND APPARATUS FOR VESSEL REPAIR IN A PATIENT

FIELD OF THE INVENTION

The present invention is related to minimally invasive thorascopically assisted replacement of the aorta. More specifically, the present invention is related to minimally invasive thorascopically assisted replacement of the descending thoracic aorta, or the abdominal portion of the aorta, utilizing a sutureless aortic graft.

BACKGROUND OF THE INVENTION

Minimal access surgical approaches to diseases of the cardiovascular system are becoming increasingly common. Traditional techniques of cardiovascular surgery are massively intrusive to the patient and induce severe trauma to the patient simply by the patient having to experience his or her chest being opened to access the heart. Furthermore, there is always the concern for blood loss in any surgery, especially heart surgery and vascular surgery. In many instances, such as the repair of an aneurysm, if angioplasty is not indicated, the cure could almost be as bad as the disease.

The present invention provides for minimally invasive surgical techniques that can quickly and simply repair a vessel, such as the aorta, so there is minimal loss of blood and minimal trauma to the patient.

SUMMARY OF THE INVENTION

The present invention pertains to an apparatus for repairing a vessel in a patient. The apparatus comprises a graft. The apparatus comprises a mechanism for compressing the vessel to the graft and holding the vessel to the graft.

The present invention pertains to a method of repairing a vessel of a patient. The method comprises the steps of placing a first end of a graft in contact with a first side of the vessel. Then there is the step of placing a second side of the graft in contact with the second side of the vessel. Next there is the step of compressing the first side of the vessel against the first end. Then there is the step of compressing the second side of the vessel against the second end.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
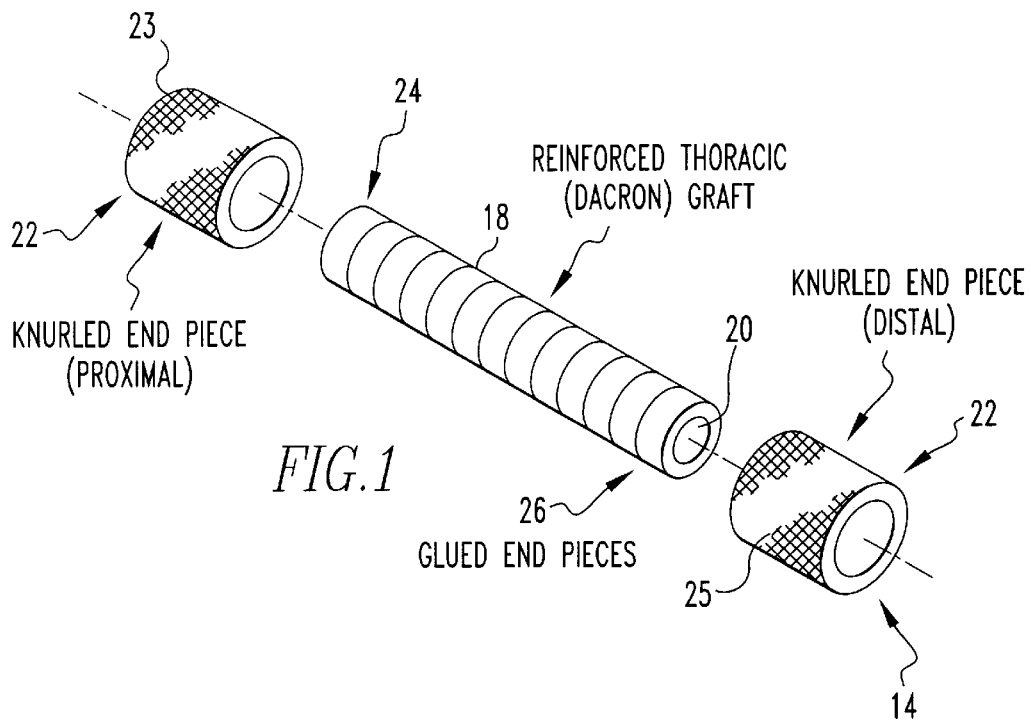
FIG. 1 is a schematic representation of a graft of an apparatus for repairing a vessel in a patient of the present invention.

Referring now to the drawings wherein like reference numerals refer to similar or identical parts throughout the several views, and more specifically to figure thereof, there is shown an apparatus 10 for repairing a vessel 12 in a patient. The apparatus 10 comprises a graft 14. The apparatus 10 comprises a mechanism 16 for compressing the vessel 12 to the graft 14 and holding the vessel 12 to the graft 14.

Preferably, the graft 14 has a first portion 18 with a flow channel 20 extending through it, and a second portion 22 connected to the first portion 18 against which the compressing mechanism comprises the graft 14. The first portion 18 is preferably flexible and can expand and contract and has an 18–25 millimeter inside diameter for placement into the thoracic artery and a 12–20 millimeter inside diameter for placement in the abdominal portion of the aorta. Preferably, the first portion 18 has a first end 24 and a second end 26 and the second portion 22 comprises a first element 23 and a second element 25. The first element 23 is disposed in proximity to the first end 24. The second element 25 is disposed in proximity to the second end.

The first end 24 preferably extends through the first element 23 and the second end 26 preferably extends through the second element 25. Preferably, the first end 24 and second end 26 are glued with adhesive to the first element 23 and second element 25, respectively. The compressing mechanism can include a first strip 28 and a second strip 30 used to compress the vessel 12 against the first element 23 and second element 25, respectively, although it is not necessary.

Preferably, the compressing mechanism includes a first tie 32 and a second tie 34 disposed about the first strip 28 and the second strip 30, respectively, to compress and hold the vessel 12 to the first end 24 and the second end 26, respectively. The first end 24 and the second end 26 are knurled or made of a metal mesh. Preferably, the first end 24 and second end 26 are made of stainless steel, and the first strip 28 and second strip 30 are made of Teflon and the first tie 32 and second tie 34 are made of plastic.

The present invention pertains to a method of repairing a vessel 12 of a patient. The method comprises the steps of placing a first end 24 of a graft 14 in contact with a first side of the vessel 12. Then there is the step of placing a second side of the graft 14 in contact with the second side of the vessel 12. Next there is the step of compressing the first side of the vessel 12 against the first end 24. Then there is the step of compressing the second side of the vessel 12 against the second end 26.

Preferably, after the first side compressing step, there is the step of securing the first side of the vessel 12 to the first end 24; and after the second side compressing step there is the step of securing the second side of the vessel 12 to the second end 26. The steps of placing the first end 24, placing the second end 26, compressing the first side, compressing the second side, securing the first side and securing the second side preferably occur within four minutes.

Preferably, the first end 24 placing step includes the step of placing the first end 24 into the first side of the vessel 12; and the second end 26 placing step includes the step of placing the second end 26 into the second side of the vessel 12. The graft 14 preferably has a first element 23 disposed about the first end 24, and the graft 14 has a second element 25 disposed about the second end 26. The first element 23 and second element 25 are made of a hard, flexible but not compressible metal mesh, which provides a complex, high-friction surface for interface with the vessel wall, and the compressing the first side step includes the step of compressing the first side against the mesh surface of the first element 23 by tightening a first strip 28 about the first side and the first element 23; and the compressing the second side step includes the step of compressing the second side against the mesh surface of the second element 25 by tightening a second strip 30 about the second side and the second element 25.

Preferably, the securing step includes the step of tying the first strip 28 with a first tie 32, and the securing the second side step includes the step of tying the second strip 30 with a second tie 34. The vessel 12 is preferably an aorta. Preferably, before the placing step there is the step of making an incision less than three inches long in the patient; and inserting the graft 14 through the incision to access the vessel 12.

In the operation of the preferred embodiment, an apparatus 10 is used to repair a vessel 12, such as a thoracic or abdominal aorta. The apparatus 10 comprises a graft 14, as shown in FIG. 1. The graft 14 has a first portion 18 which is flexible and can expand and contract with the pressure variation in the blood flow due to the pumping of the heart. The first portion 18 is made of Dacron or PTFE. At the first end 24 of the first portion 18 and the second end 26 of the first portion 18 is disposed a first element 23 and a second element 25, respectively, of a second portion 22. The first end 24 and second end 26 are made of stainless steel mesh and have a complex surface which provides a high friction contact. The first portion 18 has a flow channel 20 extending through it which allows blood to travel through the apparatus 10. The first element 23 aligns with the first end 24 of the first portion 18 so the first portion 18 extends completely through the first element 23, and the second end 26 of the first portion 18 extends completely through the second element 25, so there are minimal edges to minimize the possibility of clotting of the blood passing through the graft 14. In fact, the blood flow is at such a high rate, that there does not seem same to be any concern at all of blood clotting or any stagnation areas about the edges of the first portion 18 to allow for clotting to occur. The first element 23 and the second element 25 are glued to the first end 24 and second and, respectively, with adhesive or sutured.

The damaged vessel 12, either having been cut for a specific medical purpose, or having a section removed that was damaged due to, for instance an aneurysm, quickly has the first element 23 inserted into one side of the vessel 12 and the second element 25 inserted into the second side of the vessel 12. Speed is of the essence since blood is flowing out of the cut vessel 12 and is being lost. The graft 14 is inserted through an incision about three inches long in the chest wall without the need of a sternotomy, thoracotomy or laparotomy.

Figure 2:
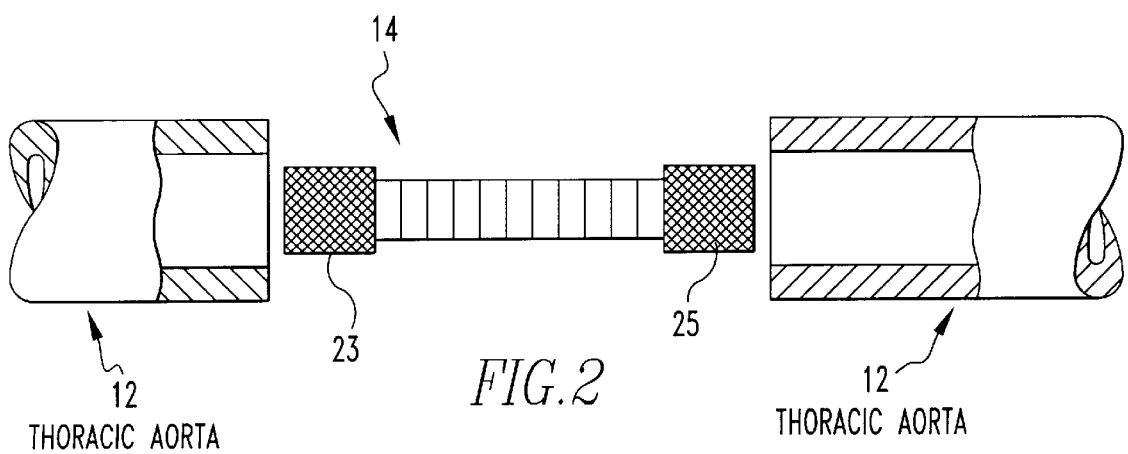
FIG. 2 is a schematic representation of the graft of the apparatus for repairing a vessel between the thoracic aorta.
Figure 3:
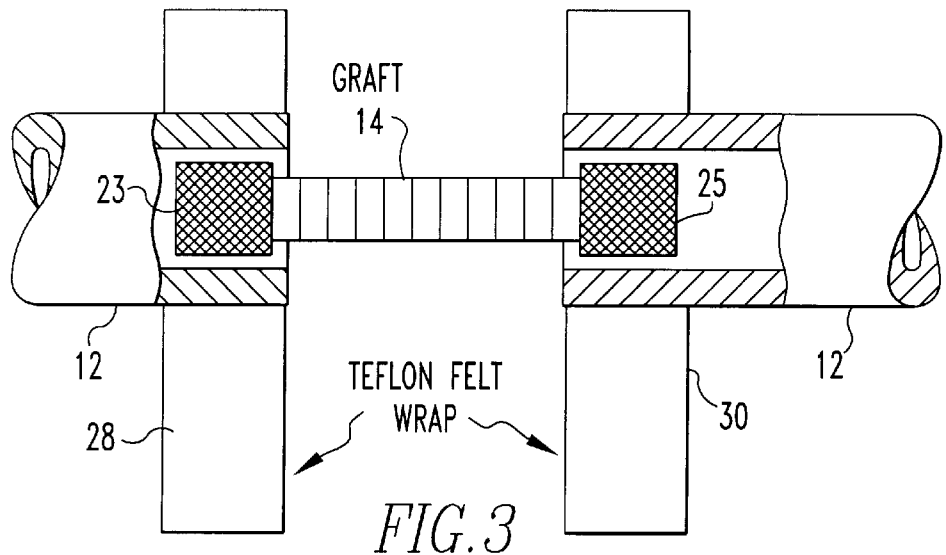
FIG. 3 is a schematic representation of the graft of the apparatus for repairing a vessel between the thoracic aorta with a first and second strip about the first and second sides of the aorta and the first and second ends of the graft, respectively.

While the incision is large enough to introduce the graft 14 to the vessel 12, there is little room or space for elaborate procedures. Once the first element 23 and second element 25 of the graft 14 are in place inside the vessel 12, as shown in FIG. 2, a first strip 28 is inserted into the incision, behind the graft 14 and back towards the incision so the first strip 28 is positioned about the vessel 12 and the first element 23. Similarly, a second strip 30 is positioned about the vessel 12 and the second element 25, as shown in FIG. 3. Alternatively, a soft backing is placed against the plastic tie-wrap, to pad the interface between the plastic tie and the aorta. The tie wrap can have teflon bonded to it which is 3–4 millimeters wide bonded to it.

Figure 4:
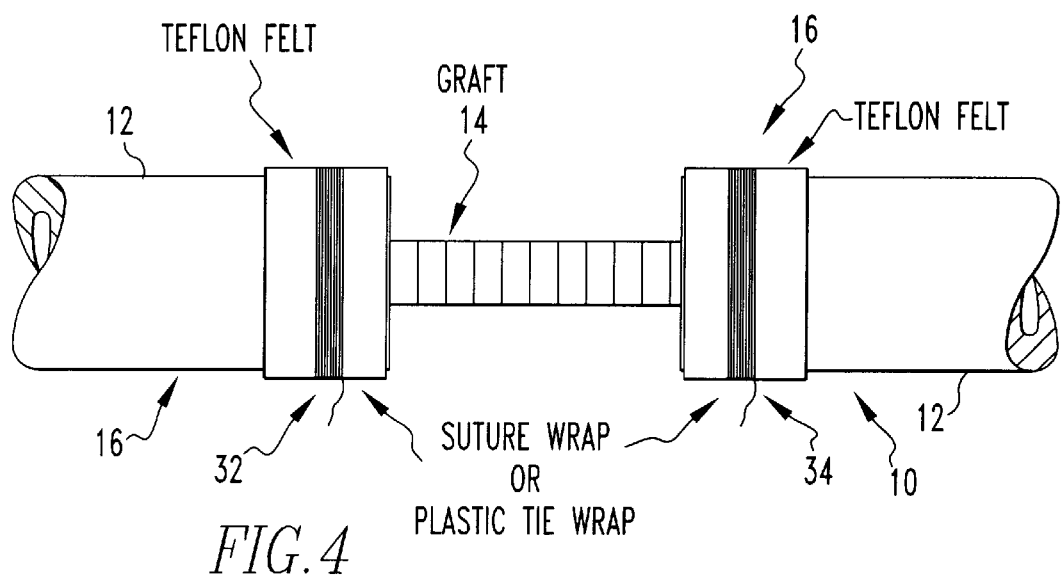
FIG. 4 is a schematic representation of the graft of the apparatus for repairing a vessel between the thoracic aorta with the first and second strips in place with first and second ties about the first and second sides of the aorta and the first and second ends of the graft, respectively.

After the first strip 28 and second strip 30 are in place, a first plastic tie and a second plastic tie are positioned about the first strip 28 and second strip 30 and tightened so the vessel 12 is compressed and secured in place against the first element 23 and second element 25, as shown in FIG. 4. The first tie 32 and second tie 34 are well known in the art and have a first end 24 that slides through a lock mechanism which prevents the first end 24 from slipping back through the lock after it is pulled through. Alternatively, the first and second strips can have hook and loop fasteners on opposing ends so when the first and second strips are tightened, the vessel 12 is compressed against the respective first element 23 and second element 25 and secured in place when the hook and loop fasteners are closed together. The mesh surface of the first element 23 and the second element 25 prevents the vessel 12 from sliding about the first and second elements. The procedure to implace the apparatus 10 can occur within 10 minutes.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for repairing a vessel in a patient comprising:
   a graft; and
   a mechanism for compressing the vessel to the graft and holding the vessel to the graft, the compressing mechanism includes a first strip and a second strip used to compress the vessel against the graft.

2. An apparatus as described in claim 1 wherein the compressing mechanism includes a first tie and a second tie disposed about the first strip and the second strip, respectively, to compress and hold the vessel to the first end and the second end, respectively.

3. An apparatus as described in claim 2 wherein the graft has a first portion with a flow channel extending through it, and a second portion connected to the first portion against which the compressing mechanism comprises the graft.

4. An apparatus as described in claim 3 wherein the first portion is flexible and can expand and contract.

5. An apparatus as described in claim 4 wherein the first portion has a first end and a second end and the second portion comprises a first element and a second element, said first element disposed in proximity to the first end, the second element disposed in proximity to the second end.

6. An apparatus as described in claim 5 wherein the first end extends through the first element and the second end extends through the second element.

7. An apparatus as described in claim 6 wherein the first end and second end are glued with adhesive or sutured to the first element and second element, respectively.

8. An apparatus as described in claim 7 wherein the first strip and the second strip used to compress the vessel against the first element and second element, respectively.

9. An apparatus as described in claim 8 wherein the first and second tie each are made of plastic and each have a soft backing attached to them.

10. An apparatus as described in claim 9 wherein the first end and the second end are knurled or made of metal or plastic mesh.

11. An apparatus as described in claim 10 wherein the first end and second end are made of stainless steel or plastic, and the first strip and second strip are made of teflon and the first tie and second tie are made of plastic.

12. A method of repairing a vessel of a patient comprising the steps of:

placing a first end of a graft in contact with a first side of the vessel;

placing a second end of the graft in contact with the second side of the vessel;

compressing the first side of the vessel against the first end with a first strip; and compressing the second side of the vessel against the second end with a second strip.

13. A method as described in claim 12 wherein after the first side compressing step there is the step of securing the first side of the vessel to the first end; and after the second side compressing step there is the step of securing the second side of the vessel to the second end.

14. A method as described in claim 13 wherein the steps of placing the first end, placing the second end, compressing the first side, compressing the second side, securing the first side and securing the second side occur within 10 minutes.

15. A method as described in claim 14 wherein the first end placing step includes the step of placing the first end into the first side of the vessel; and the second end placing step includes the step of placing the second end into the second side of the vessel.

16. A method as described in claim 15 wherein the graft has a first element disposed about the first end, and the graft has a second element disposed about the second end, said first element and second element made of a hard, flexible but not compressible metal mesh, which provides a complex, high-friction surface for interface with the vessel wall, and the compressing the first side step includes the step of compressing the first side against the mesh surface of the first element by tightening the first strip about the first side and the first element; and the compressing the second side step includes the step of compressing the second side against the knurled surface of the second element by tightening the second strip about the second side and the second element.

17. A method as described in claim 15 wherein the securing step includes the step of tying the first strip with a first tie, and the securing the second side step includes the step of tying the second strip with a second tie.

18. A method as described in claim 16 wherein the vessel is an aorta.

19. A method as described in claim 17 wherein before the placing step, there is the step of making an incision less than three inches long in the patient; and inserting the graft through the incision to access the vessel.

* * * * *